United States Patent [19]

Knuuttila et al.

[11] Patent Number: 4,914,251

[45] Date of Patent: Apr. 3, 1990

[54] CATALYST SYSTEM FOR ALKYLATING ALKYL AROMATICS WITH OLEFINS, PROCEDURE FOR PREPARING THE CATALYST, AND PROCEDURE FOR CARRYING OUT THE ALKYLATING

[75] Inventors: Pekka Knuuttila, Porvoo; Aila Ali-Hokka, Kulloo, both of Finland

[73] Assignee: Neste OY, Finland

[21] Appl. No.: 309,680

[22] Filed: Feb. 10, 1989

[51] Int. Cl.[4] .......................... C07C 5/393; C07C 2/64
[52] U.S. Cl. ...................................... 585/453; 585/452; 502/174
[58] Field of Search ................. 585/452, 453; 502/174

[56] References Cited

U.S. PATENT DOCUMENTS 3,291,752 12/1966 Hamblino et al. ................ 502/174

FOREIGN PATENT DOCUMENTS

| 61-227536 | of 1986 | Japan ................................ 585/453 |
| 531358 | of 1941 | United Kingdom ................ 502/174 |
| 1269280 | of 1972 | United Kingdom . |

*Primary Examiner*—Sneed Helen M. S.
*Assistant Examiner*—J. Saba
*Attorney, Agent, or Firm*—Steinberg & Raskin

[57] ABSTRACT

The present invention concerns a catalyst for alkylation of alkyl aromatics with olefins, i.e. alkylating toluene, a procedure for the production of the catalyst, and a procedure for carrying out the alkylating of the toluene. The catalyst system contains sodium oxide ($Na_2O$) on a potassium carbonate ($K_2CO_3$) carrier, preferably at about 10 to 70%.

16 Claims, 1 Drawing Sheet

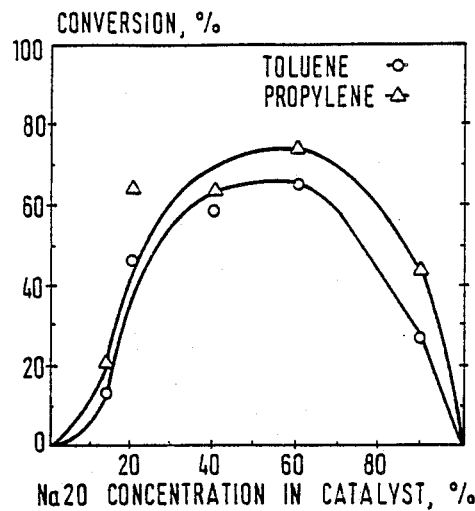
FIG. 1 CONVERSION OF TOLUENE AND PROPYLENE INTO PRODUCTS AS A FUNCTION OF THE SODIUM OXIDE CONCENTRATION OF THE CATALYST.
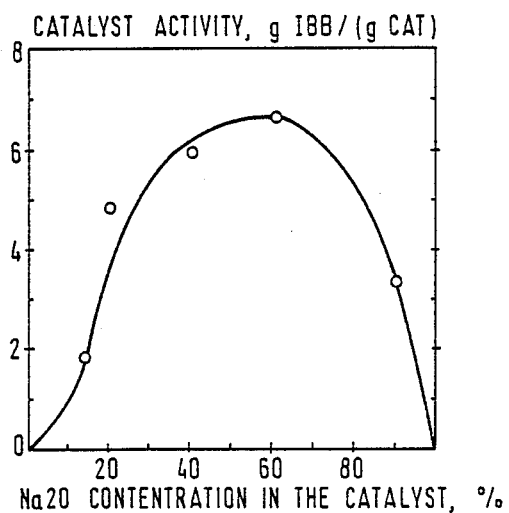
FIG. 2 CATALYST ACTIVITY WITH REFERENCE TO ISOBUTYL BENZENE PRODUCTION ON VARIOUS SODIUM OXIDE CONCENTRATIONS OF THE CATALYST.

CATALYST SYSTEM FOR ALKYLATING ALKYL AROMATICS WITH OLEFINS, PROCEDURE FOR PREPARING THE CATALYST, AND PROCEDURE FOR CARRYING OUT THE ALKYLATING

BACKGROUND OF THE INVENTION

The present invention concerns a catalyst system for alkylating alkyl aromatics, e.g. for alkylating toluene, a procedure for preparing the catalyst system, and a procedure for carrying out the alkylation of the alkyl aromatics, i.e. alkylating toluene.

Alkaline metal catalysts well-suited for side-chain alkylation of alkyl aromatics with olefins are known in the art, in which the metallic sodium or potassium has been dispersed onto the surface of an inorganic or graphite carrier. For instance, in the Neste Finnish Patent Application No. 865,362, a catalyst system is disclosed which contains metallic sodium on a $K_2CO_3$ carrier. A catalyst is known from British Patent No. 1,269,280, which is produced by dispersing sodium and/or lithium on a nonaqueous potassium compound. Additionally, reference is made to the Neste Finnish Patent Application No. 865,363, in which the catalyst system used contains metallic sodium dispersed thermally from a sodium-containing compound onto a surface of a solid $K_2CO_3$.

However, drawbacks of such catalysts include cumbersome manufacturing and processing of the catalysts, a relatively low activity at high temperatures, and rapid decrease of activity as a consequence of the catalysts becoming tarred and coked.

SUMMARY OF THE INVENTION

Accordingly, it is an object of the present invention to improve over the above-noted catalytic systems of the prior art, eliminating the drawbacks noted above with respect thereto.

It is also an object of the present invention to improve the ease with which an appropriate catalyst system for alkylating alkyl aromatics with olefins, can be prepared.

It is another object of the present invention to provide a catalyst for alkylating of alkyl aromatics with olefins, having improved activity.

These and other objects are attained by the present invention which is directed to a catalyst for alkylating alkyl aromatics with olefins, the catalyst comprising sodium oxide on a potassium carbonate carrier. The present invention is also directed to a method for producing such a catalyst, which comprises the step of mixing the sodium oxide and the potassium carbonate. The present invention is furthermore directed to a method for the alkylation of alkyl aromatics with olefins, comprising the steps of carrying out the alkylation in the presence of a catalyst system comprising sodium oxide on a potassium carbonate carrier.

The catalyst of the present invention represents improvement in comparison with the above-noted catalysts of the prior art, in that the starting materials are easier to process and yet the catalyst is as active as the alkali metal catalyst.

The catalyst system of the present invention contains sodium oxide ($Na_2O$) on a potassium carbonate ($K_2CO_3$) carrier. The sodium oxide concentration is preferably about 10 to 70%, more preferably about 40 to 60%.

The procedure for producing the catalyst system of the present invention is characterized in that the catalyst system is manufactured by mixing sodium oxide ($Na_2O$) and potassium carbonate ($K_2CO_3$). Preferably, the quantity of sodium is about 10 to 70%, more preferably about 40 to 60%, in the mixing thereof with the potassium carbonate.

The procedure for alkylating toluene is characterized by the catalyst system utilized for carrying out this alkylation being composed of sodium oxide ($Na_2O$) on a potassium carbonate ($K_2CO_3$) carrier. Preferably, the sodium oxide concentration of the catalyst system is about 10 to 70%, more preferably about 40 to 60%.

The production of the catalyst of the present invention is carried out in a simple manner by mixing sodium oxide in potassium carbonate, and by heating the mixture. The heating may take place at 100° to 400° C. temperature, but most advantageous and rapidly the heating takes place at 260° to 280° C. temperature, with a preferable heating period being about 0.5 to 1 hour. The heating is carried out advantageously, but not necessarily, in a vacuum.

It is surprising that the catalyst of the present invention may be active, since neither sodium oxide nor potassium carbonate alone displays any activity, and no chemical reactions take place between the potassium carbonate and the sodium oxide, as evidenced by the fact that in the X-ray diffraction analysis of the completed catalysts, the intended phases, i.e., sodium oxide and potassium carbonate, were identified.

BRIEF DESCRIPTION OF THE DRAWINGS

The present invention will now be described in greater detail below, with reference to preferred embodiments thereof illustrated in the accompanying drawings, in which FIG. 1 is a graph of alkylating conversion as a function of catalyst concentration in accordance with the present invention, and FIG. 2 is a graph of catalyst activity as a function of catalyst concentration in accordance with thee present invention.

DESCRIPTION OF THE PREFERRED EMBODIMENTS

The catalysts of the present invention were tested with propylene by side-chain-alkylating toluene.

The alkylating reaction can be illustrated with the following reaction equation:

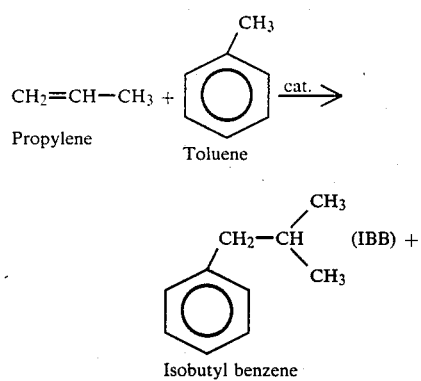

-continued

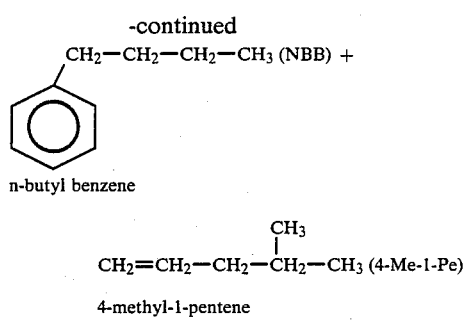

n-butyl benzene $$CH_2=CH_2-CH_2-\overset{\overset{\displaystyle CH_3}{|}}{CH_2}-CH_3 \text{ (4-Me-1-Pe)}$$

4-methyl-1-pentene

The main product produced in the reaction is isobutyl benzene; n-butyl benzene and a dimerization product of propylene, 4-methyl-1-pentene, are produced as by-products as a result of by-reactions.

The tests were carried out in a 1 dm³ autoclave and in a continuous-action microreactor.

After the reaction, the gas and liquid phases were analyzed by gas-chromatography.

The invention is described in detail below with the aid of a catalyst production example and an alkylating example. However, the present invention is not intended to be restricted to the details thereof.

CATALYST PRODUCTION

The catalyst was produced in a 1 dm³ Parr steel reactor at 270° C. temperature and in a vacuum. The desired amounts of sodium oxide and potassium carbonate were weighed into the reactor, which was closed, and the vacuum was established. The mixture was heated to 260° to 280° C., at which it was maintained for 0.5 to 1.0 h.

Seven catalysts were prepared, with the sodium content varying from 0 to 100 percent by weight.

ANALYZING CATALYSTS

The completed catalysts were dark grey or brownish in color. When producing catalyst containing sodium oxide of 14 to 90% by weight, a metallic phase could be observed on the walls of the reactor. Of the completed catalysts, a catalyst containing 40% by weight sodium oxide was analyzed using an X-ray diffraction metric method (XRD). The phases identified in the diffraction analysis that were present in the catalyst, were sodium oxide, potassium carbonate, and probably metallic sodium. The sodium oxide had large crystals and its concentration was high. Potassium carbonate had either small crystals or it was coated by sodium oxide because the peaks were low in intensity and wide.

TESTING THE CATALYSTS

The catalysts were tested by side-chain alkylating toluene with propylene. The tests were carried out in a 1 dm³ Parr autoclave and in a continuous-action microreactor.

TESTS IN A CHARGE REACTOR

The following were selected for the reaction conditions: reaction time t =19 h; reaction temperature T =175° C.; toluene/propylene molar ratio n(T)n(P) =0.7; catalyst mass m =23.0g.

The catalyst was loaded into the reactor under nitrogen atmosphere. The reactor was closed and vacuum was produced. Toluene was conducted into the reactor with the aid of the vacuum prevailing in the reactor through a valve in the reactor cover. Propylene was supplied in liquid form into the reactor.

After the reaction (175° C., 19 h), the gas and liquid phases were analyzed by gas-chromatography.

RESULT OF CHARGE EXPERIMENTS

Isobutyl benzene (IBB) was obtained as the main product in the reaction. The product mixture also contained n-butyl benzene (NBB), 4-methyl-1-pentene (4M1P) as a dimerization product of the propylene, isomerization products of the 4M1P, and various hexene isomers, as a result of the by-reactions.

A summary of the results of the test runs is presented in Table 1. From the composition of the product, the conversions of the starting materials into products, the formation selectivities of various product components, and the activity of the catalyst regarding the IBB production were calculated. The conversion of the toluene and propylene into products as a function of the sodium oxide concentration contained in the catalyst, is presented in FIG. 1. The activity of the catalyst in grams of IBB per catalyst gram g IBB/ (g cat.)), is presented in FIG. 2.

TABLE 1

Summary of the test runs with the $Na_2O/K_2CO_3$ catalyst.

| Catal. $Na_2O$ % by w. | Conversions tol. % | prop. % | Selectivities IBB % | NBB % | 4MIP % | ISOM. % | IBB/ NBB ratio mol/ mol | Cat. act. g IBB/g cat. |
|---|---|---|---|---|---|---|---|---|
| 0 | 0.0 | 0.0 | 0.0 | 0.0 | 0.0 | 0.0 | — | 0.0 |
| 14 | 13.4 | 20.7 | 68.4 | 6.2 | 8.4 | 4.0 | 11 | 1.8 |
| 20 | 46.2 | 64.0 | 66.4 | 7.4 | 4.8 | 8.0 | 9 | 4.8 |
| 40 | 58.4 | 63.5 | 71.7 | 7.5 | 4.7 | 8.7 | 10 | 6.0 |
| 60 | 64.8 | 73.8 | 70.9 | 7.1 | 3.5 | 9.1 | 10 | 6.6 |
| 90 | 26.5 | 43.7 | 72.8 | 8.3 | 6.6 | 7.7 | 9 | 3.3 |
| 100 | 0.0 | 0.0 | 0.0 | 0.0 | 0.0 | 0.0 | — | 0.0 |

IBB = isobutyl benzene, NBB = n-butyl benzene, 4MIP = 4-methyl-1-pentene, ISOM = isomerization products of 4MIP It is observed from Table 1 and FIGS. 1 and 2, that the conversion as well as the activity of the starting materials are best with a catalyst in which the sodium concentration is 60% by weight. However, the results are not significantly poorer with catalysts containing sodium oxide of 20 or 40% by weight.

When the $Na_2O/K_2CO_3$ catalyst is compared with a catalyst which is prepared from a pure alkali metal and alkaline metal carbonate (6% $Na/K_2CO_3$), the results are remarkably better with a 20, 40 and 60% oxide catalyst, in comparing the conversions and the activities of the catalysts. With the $Na/K_2CO_3$ catalyst in test runs carried out under the same conditions, the toluene conversion is 30%, the propylene conversion is 42%, and the activity of the catalyst is 4 to 5 g IBB/(g cat), while the conversions with catalysts containing 20 to 60% by weight sodium oxide are 46 to 65% in toluene conversion, 64 to 74% in propylene conversion, and the activity of the catalyst is 5 to 7 g IBB/(g cat).

Additionally, it was observed that the oxide catalysts becomes readily activated, and no induction time was noted in the reaction. In other words, the pressure in the reaction started to fall immediately after the temperature had risen to 175° C. The starting of the reaction took about one hour with the alkaline metal catalyst instead.

A significant difference between the alkaline metal catalyst and the oxide catalyst is the high isomerization efficiency of the 4M1P in the oxide catalyst. The formation selectivity of the isomerization products of the 4M1P with the oxide catalysts is about doubled as compared with the alkaline metal catalyst. However, the isomerization may be reduced by lowering the reaction temperature and shortening the reaction time.

CONTINUOUS-ACTION REACTOR

A 40% $Na_2O/K_2CO_3$ catalyst was selected for a continuous-action microreactor run. The parameters of the run were as follows: toluene feed about 9 g/h; propylene feed about 20 g/h; reactor temperature 170° C. and reactor pressure 90 bar. 26 g of the catalyst was loaded.

The $Na_2O/K_2CO_3$ catalyst appeared to be especially suitable for producing isobutyl benzene in a continuous-action reactor because its tar formation (products heavier than NBB) is especially low. The proportion of tars is not increased either, with temperature increase and catalyst ageing. Although the $Na_2O/K_2CO_3$ catalyst in rather finely powdered, no pressure losses can be observed in the reactor because the tarring of the catalyst is non-existent. Therefore, the temperature of the reactor can be raised up to 200° C. A drawback in the $Na_2O/K_2CO_3$ catalyst, is its tendency to produce 4-methyl-2-pentene as a main dimerization product. Such isomerization tendency is strongly dependent on the temperature. The lowering of the temperature to 150° C. returns the isomerization close to the isomerization ratio characteristic of the $Na/K_2CO_3$ catalyst.

TABLE 3

| Microreactor run with 40% $Na_2O/K_2CO_3$ catalyst | | | | | | | |
|---|---|---|---|---|---|---|---|
| Run time (h) | Tol. conv. (%) | Selectivities (%) | | | | Producton h/g cat. | |
| | | 4MlP | other hex. | IBB | NBB | 4MlP | IBB |
| 73 | 48.6 | 32.6 | 11.0 | 49.0 | 6.6 | 0.15 | 0.23 |
| 162 | 32.8 | 23.0 | 8.0 | 57.1 | 5.2 | 0.07 | 0.16 |
| 260 | 10.0 | 17.8 | 7.3 | 63.9 | 5.5 | 0.05 | 0.16 |

The preceding description of the present invention is merely exemplary, and is not intended to limit the scope thereof in any way.

What is claimed is:

1. Catalyst for alkylation of an alkyl aromatic, said catalyst comprising sodium oxide on a potassium carbonate carrier.

2. The catalyst of claim 1, having a sodium oxide concentration of about 10 to 70%.

3. The catalyst of claim 2, wherein the sodium oxide concentration is about 40 to 60%.

4. Method for producing a catalyst for alkylating an alkyl aromatic, said catalyst comprising sodium oxide on a potassium carbonate carrier, comprising the step of
   mixing the sodium oxide and the potassium carbonate.

5. The method of claim 4, wherein about 10 to 70% of the sodium oxide is mixed with about 90 to 30% of the potassium carbonate.

6. The method of claim 5, wherein about 40 to 60% of the sodium oxide is mixed with about 60 to 40% of the potassium carbonate.

7. The method of claim 4, comprising the additional step of
   heating the resulting mixture of sodium oxide and potassium carbonate at about 100 to 400° C.

8. The method of claim 7, wherein the resulting mixture is heated to a temperature at about 260°–280° C.

9. The method of claim 8, wherein said resulting mixture is heated from about ½ to 1 hour.

10. The method of claim 9 wherein said heating is carried out under vacuum.

11. Method for alkylation of an alkyl aromatic, comprising the step of reacting an alkyl aromatic with an alkylating agent in the presence of a catalyst system comprising sodium oxide on a potassium carbonate carrier.

12. The method of claim 11, wherein said catalyst system comprises about 10 to 70% of the sodium oxide.

13. The method of claim 12, wherein said catalyst system comprises about 40 to 60% of the sodium oxide.

14. The method of claim 11, wherein said alkyl aromatic is toluene.

15. The method of claim 14, wherein said alkylating agent is propylene.

16. The method of claim 11, wherein said alkylating agent is an olefin.

* * * * *